US011420909B2

United States Patent
Kartouzian et al.

(10) Patent No.: US 11,420,909 B2
(45) Date of Patent: Aug. 23, 2022

(54) METHOD FOR ENANTIOMERIC ENRICHMENT

(71) Applicant: TECHNISCHE UNIVERSITÄT MÜNCHEN, Munich (DE)

(72) Inventors: Aras Kartouzian, Munich (DE); Ulrich Heiz, Munich (DE); Farinaz Mortaheb, Munich (DE); Katrin Oberhofer, Eching (DE); Johann Riemensberger, Eching (DE); Hristo Iglev, Garching (DE); Reinhard Kienberger, Garching (DE)

(73) Assignee: TECHNISCHE UNIVERSITÄT MÜNCHEN, Munich (DE)

(*) Notice: Subject to any disclaimer, the term of this patent is extended or adjusted under 35 U.S.C. 154(b) by 40 days.

(21) Appl. No.: 17/259,962

(22) PCT Filed: Jul. 17, 2019

(86) PCT No.: PCT/EP2019/069278
§ 371 (c)(1),
(2) Date: Jan. 13, 2021

(87) PCT Pub. No.: WO2020/016316
PCT Pub. Date: Jan. 23, 2020

(65) Prior Publication Data
US 2021/0309585 A1 Oct. 7, 2021

(30) Foreign Application Priority Data
Jul. 18, 2018 (DE) .................. 10 2018 117 346.6

(51) Int. Cl.
C07B 57/00 (2006.01)
C07C 37/68 (2006.01)
G01N 21/19 (2006.01)

(52) U.S. Cl.
CPC ............ *C07B 57/00* (2013.01); *C07C 37/685* (2013.01); *G01N 21/19* (2013.01)

(58) Field of Classification Search
CPC ..... C07B 2200/07; C07B 57/00; C07B 53/00; C07B 2200/13; C07B 2200/05;
(Continued)

(56) References Cited

U.S. PATENT DOCUMENTS

2008/0200441 A1* 8/2008 Brinton ................. A61K 31/05
514/681
2008/0207944 A1 8/2008 Seidel-Morgenstern et al.
(Continued)

FOREIGN PATENT DOCUMENTS

| CN | 101297020 B | * | 10/2012 | ........... C09K 19/586 |
| WO | WO-2017003909 A2 | * | 1/2017 | .............. B01L 3/502 |
| WO | WO-2018081243 A1 | * | 5/2018 | ................ G01J 1/16 |

OTHER PUBLICATIONS

Nguyen, Lien Ai; He Hua; Pham-Huy, Chuong: Chrial Drugs. An Overview. In: International Journal of Biomedical Science, Bd. 2, 2006, H. 2, S. 85-100.—ISSN 1550-9702 9 (p); 1555-2810 (e). URL: https://www.ncbi.nlm.nih.gov/pmc/articles/PMC3614593/pdf/IJBS-2-85.pdf [abgerufen am Nov. 27, 2018].

*Primary Examiner* — Michael P Stafira
(74) *Attorney, Agent, or Firm* — Caldwell Intellectual Property Law

(57) ABSTRACT

According to the present invention there is provided a method for enantiomeric enrichment of a mixture of two enantiomers of a chiral compound, the method comprises the application of the mixture of two enantiomers of a chiral compound onto a surface of a support material for producing a coated support, the determination a first value of an optical activity ($OA_0$) of the coated support, the irradiation of the coated support with a light beam having an intensity at least higher than a desorption threshold of one of the enantiomers (Continued)

from the coated support, wherein, if the support material is achiral, the light beam is circularly polarized and, if the support material is chiral, the light beam is unpolarized, linearly polarized or circularly polarized, and the determination of a second value of the optical activity ($OA_e$) of the coated support after said irradiation, wherein the second value of the optical activity ($OA_e$) differs from the first value of the optical activity ($OA_0$).

20 Claims, 3 Drawing Sheets

(58) Field of Classification Search
CPC ....... C07B 63/00; C07B 41/02; C07B 59/002; C07B 35/02; C07B 63/04; C07B 43/04; C07B 37/04; C07B 63/02; C07B 55/00; C07B 2200/09; C07B 59/001; G01N 33/507; G01N 21/3586; G01N 22/00; G01N 33/15; G01N 21/19; G01N 23/20075; G01N 27/44747; G01N 30/02; G01N 1/40; G01N 1/405; G01N 1/4077; G01N 11/02; G01N 2011/0006; G01N 2333/47; G01N 2333/912; G01N 2440/14; G01N 2500/02; G01N 2500/04; G01N 2500/10; G01N 27/40; G01N 2800/52; G01N 30/482; G01N 33/5017; G01N 33/5058; G01N 33/54353; G01N 33/5438; G01N 33/573; G01N 33/574; G01N 33/6863; G01N 33/6893; G01N 33/74; G01N 33/5008; G01N 33/542; G01N 33/581
See application file for complete search history.

(56) References Cited

U.S. PATENT DOCUMENTS

2009/0296744 A1* 12/2009 Dantus .................. G01N 21/21
372/27
2015/0187558 A1* 7/2015 Mills ..................... G01N 33/49
250/288

* cited by examiner

METHOD FOR ENANTIOMERIC ENRICHMENT

CROSS-REFERENCE TO RELATED APPLICATIONS

This application is a national phase application of International Application Serial No. PCT/EP2019/069278, filed on Jul. 17, 2019 and entitled "METHOD FOR ENANTIOMERIC ENRICHMENT," which claims priority to German application Serial No. DE 10 2018 117 346.6, filed on Jul. 18, 2018 and entitled "VERFAHREN ZUR ENANTIOMERENANREICHERUNG." Each of International Application Serial No. PCT/EP2019/069278 and German application Serial No. DE 10 2018 117 346.6 is incorporated by reference herein in its entirety.

FIELD OF THE INVENTION

The present invention relates to a method for enantiomeric enrichment, and more particularly to a novel method for enantiomeric enriching a mixture of two enantiomers of a chiral compound using optical means.

BACKGROUND

Enantiomers are molecules that are identical in atomic constitution and bonding, but that differ in the 3D arrangement of their atoms so that they are mirror images of each other. Usually the two enantiomers are referred to as L- and D-enantiomers or S- and R-enantiomers. The separation of enantiomers and the enrichment of their mixtures is rather challenging, since they have identical chemical properties unless in a chiral environment and possess identical physical properties unless while interacting with polarized light.

Separation of enantiomers of chiral molecules is an important step in various disciplines such as pharmaceutical industry, cosmetic industry and biotechnology. The separation of enantiomers is of great interest specifically to the pharmaceutical industry since more than 50% of pharmaceutically active ingredients are chiral, and 9 of the top 10 drugs with respect to worldwide sales value have chiral active ingredients. Although they have the same chemical structure, enantiomers of most chiral ingredients exhibit marked differences in biological activities such as for example in pharmacology, toxicology, pharmacokinetics, metabolism. Therefore, it is important to promote the enantiomeric enrichment of racemic drugs (having an equimolar mixture of two enantiomers) in the pharmaceutical industry as well as in clinic in order to reduce the amount of the unwanted enantiomer in the mixture (i.e. enriching the mixture) or to fully eliminate the unwanted enantiomer from the mixture (i.e. separating the unwanted enantiomer). Further, it is desired to find an optimal treatment and a right therapeutic control for the patient (Nguyen L A, He H, Pham-Huy C. Chiral Drugs: An Overview; International Journal of Biomedical Science: IJBS. 2006; 2(2):85-100.).

One common approach of enantiomeric enrichment of a mixture of two enantiomers of a chiral compound is to chemically convert the enantiomers into species that can be separated by forming diastereomers. Unlike enantiomers, diastereomers have entirely different physical properties (for example boiling point, melting point, NMR shifts, solubility) so that they become separable by conventionally employed means, such as chromatography and crystallization.

Another common method for separation of a mixture of enantiomers without forming diastereomers is to use chromatography on a chiral stationary phase providing a chiral environment. In this case, the different interaction of the enantiomers with the column material leads to their separation.

US patent publication number 2008/0207944 A1 discloses a method for separating compound-forming chiral systems. The method provides for a hybrid process which comprises an enrichment step including a chromatographic method or an enantioselective membrane, and the step of crystallization using supramolecular complexes.

One of the drawbacks, or limitations, of the known separation methods is that these methods inter alia include the interaction with and/or the addition of foreign chemical compounds which have to be removed after enantiomeric enrichment of the mixture. For instance, in the pharmaceutical industry these foreign chemical compounds need to be strictly avoided.

The object underlying the present invention is to provide a method for enantiomeric enrichment of a mixture of two enantiomers by minimizing the use of foreign chemical compounds (e.g. chemical reagents), which in turn leads to a reduction of the risk of contamination of the enantiomerically enriched mixture. This object is solved by the method of claim 1.

SUMMARY OF THE DISCLOSURE

According to the present invention there is provided a method for enantiomeric enrichment of a mixture of two enantiomers of a chiral compound using optical means, thereby minimizing the use of foreign chemical compounds. The method comprises the steps of a) applying the mixture of two enantiomers of a chiral compound onto a surface of a support material for forming a coated support; b) determining a first value of optical activity ($OA_0$) of the coated support; c) irradiating, via an optical means, the coated support with a light beam having an intensity at least higher than a desorption threshold of one of the enantiomers from the coated support, wherein, if the support material is achiral, the light beam is circularly polarized and, if the support material is chiral, the light beam is unpolarized, linearly polarized, elliptically polarized or circularly polarized; and d) determining a second value of the optical activity ($OA_e$) of the coated support after said irradiating, for determining the level of enantiomeric enrichment.

As used herein the term "value of optical activity" refers to either the anisotropy factor g or the optical rotation of the coated support. The anisotropy factor is generally determined by equation (1), reading as follows:

$$g = \frac{X_{LCP} - X_{RCP}}{\left(\frac{X_{LCP} - X_{RCP}}{2}\right)} \tag{1}$$

wherein the parameters $X_{LCP}$ and $X_{RCP}$ represent one of the optical absorption, second harmonic generation, and scattering cross-section of the coated support, while interacting with left circularly polarized (LCP) light and right circularly polarized (RCP) light, respectively.

The optical rotation is defined as the angle between the polarization planes of the linearly polarized light incoming to the coated support and the linearly polarized light leaving the coated support.

According to the method of the present invention, the coated support is irradiated with a light beam having an intensity which is at least higher than a desorption threshold of one of the enantiomers from the coated support. As is known to those skilled in the art, the desorption threshold of a compound from a surface is a property that depends on the interactions of the compound with the surface and the light beam used for irradiation. The value of desorption threshold therefore varies for different combinations of compounds, support materials and light beams. Similarly, the desorption threshold of a chiral compound from a coated support material varies with the choice of chiral compound, the support material and the light beam that is used for irradiation. Methods for determining whether the intensity of the light beam lies above the desorption threshold are known to those skilled in the art and, as such, one example thereof will be presented here. For instance, the optical absorbance of a reference coated support is measured before irradiation and after irradiation. If the intensity of the light beam used for irradiation lies above the desorption threshold, a reduction in optical absorbance will be observed. If no such reduction is observed, the intensity of the light beam is increased incrementally. These steps will be repeated until a decrease in optical absorbance of the reference coated support upon irradiation is observed.

According to the present invention, a sense of asymmetry is introduced in the system for promoting an enantiomeric enrichment a preferential desorption of the enantiomers, i.e. for desorbing one enantiomer with a higher rate than the other. To this end, at least one of the support material or the light beam should provide asymmetric interaction with the two enantiomers. Accordingly, the support material should be chiral and/or the light beam should be circularly polarized. If asymmetry of the system is provided by a chiral support material, the polarization of the light beam is not restricted.

In a preferred embodiment of the present invention, the method further comprises repeating said steps of irradiating the coated support and said determining the optical activity thereof until a final (desired) value of the optical activity $(OA_f)$ of the coated support is achieved. The value of the final (desired) optical activity depends on the desired level of enrichment. By comparing the value of the optical activity of the mixture with the optical activity of the enantiomerically pure substances, the absolute level of enrichment, i.e. the enantiomeric excess of the mixture, can be determined. The maximum level of enrichment according to the present invention pertains to the value of the optical activity that remains constant upon further irradiation.

In a preferred embodiment of the present invention, the light beam has a wavelength that matches resonantly with an absorption band of the chiral compound either by a single photon or by multiple photons. Tuning the wavelength of the light beam to resonantly match with an absorption band of the chiral compound, the interaction of the light beam with the coated support is advantageously enhanced.

In a preferred embodiment of the present invention, said irradiating step is provided for a duration between 0.2 ns and 1000 s.

In a preferred embodiment of the present invention, said irradiating comprises irradiating the coated support by a light emitting diode (LED), a pulsed laser or a continuous wave laser.

In a preferred embodiment of the present invention, said determining the optical activity of the coated support includes determining the optical activity by one of circular dichroism measurement, optical rotation dispersion measurement, second harmonic generation circular dichroism measurement or second harmonic generation optical rotation measurement.

In a preferred embodiment of the present invention, the applying of the mixture of two enantiomers onto the support material includes one of the methods of molecular evaporating, spin coating, dip coating and drop casting.

In a preferred embodiment of the present invention, the chiral support material belongs to the group of high Miller index surfaces of metals such as (643) and (531) surfaces.

Alternatively, in a preferred embodiment of the present invention, the achiral support material belongs to the group of amorphous solids or low Miller index surfaces of a metal such as (111) and (110) surfaces.

In a preferred embodiment of the present invention, the mixture of the two enantiomers is provided in powder or liquid form.

Embodiments of the present invention apply a physical approach using optical means for enantiomeric enrichment of a mixture of the two enantiomers, thereby providing the desirable benefit of significantly reducing the addition of foreign chemical compounds.

BRIEF DESCRIPTION OF THE DRAWINGS

The non-limiting embodiments of the present invention will be more fully appreciated by reference to the accompanying drawings, in which.

DETAILED DESCRIPTION

Reference will now be made to non-limiting embodiments of a method according to the present invention. It should be understood by those skilled in the art that other modifications and equivalents will be evident in view of the non-limiting embodiments disclosed herein and that such variants should be considered to be within the scope of the present invention.

Figure 1:
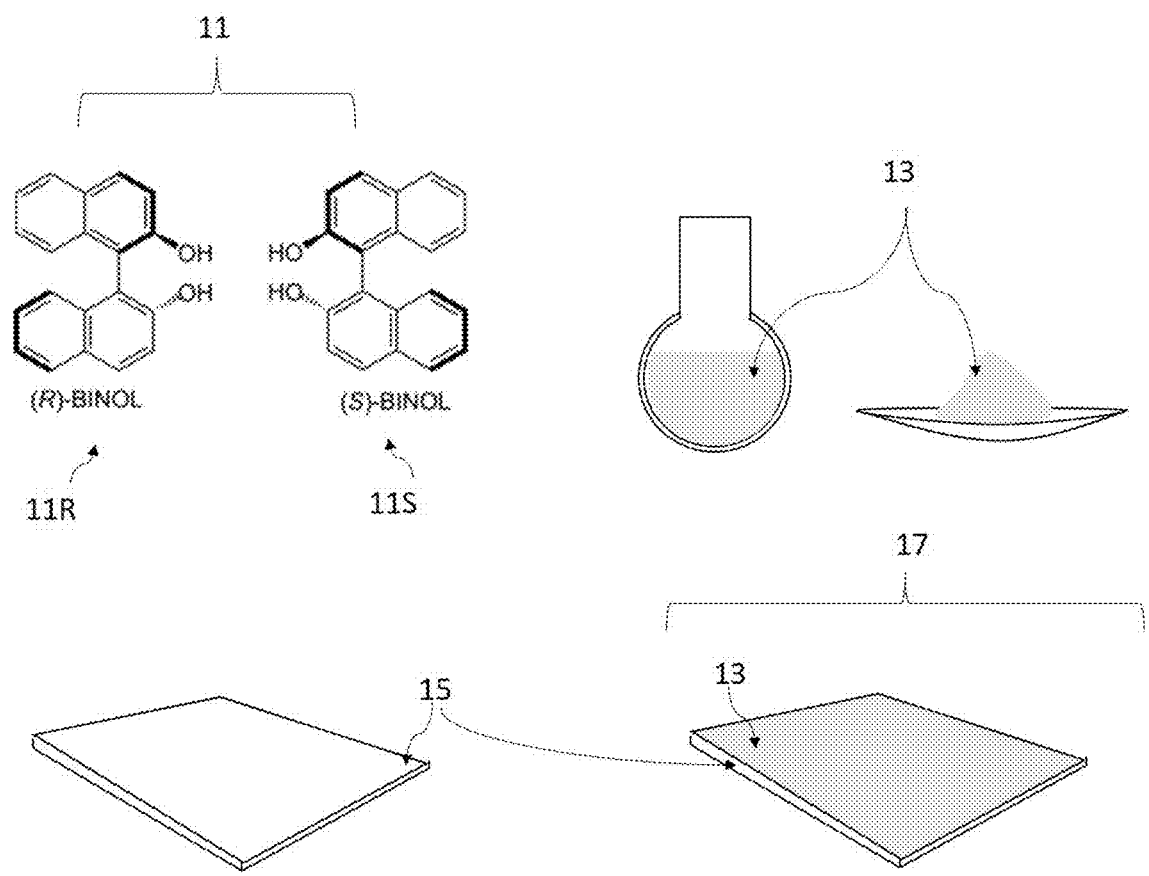
FIG. 1 shows a schematic illustration of a mixture of two enantiomers and a support material according to embodiments of the present invention.

FIG. 1 illustrates an example of components to produce a coated support (17) according to the present invention. As an example of a chiral compound (11), BINOL is shown with its two enantiomers R-BINOL and S-BINOL (11R, 11S). A mixture (13) of the chiral compound may be in the form of a solution or powder. The composition of the mixture (13) of the enantiomers may have all the combinations of mole fractions between the two enantiomers with an enantiomeric excess (ee) in the range of $0 \leq ee < 1$. A racemic mixture containing equal amounts of the two enantiomers has an ee of 0, while one single pure enantiomer of the chiral compound has an ee of 1. As it will be appreciated by those skilled in the art, a pure enantiomer cannot be enantiomerically enriched any further.

A support material (15) may be chiral including, but not limited to, high Miller index metal surfaces such as (643) and (531) surfaces. Support material (15) may be achiral including, but not limited to, low Miller index metal surfaces such as (100), (110) and (111) surfaces, or non-crystalline such as glass and amorphous metal surfaces. A coated support (17) according to the present invention, is produced by applying the mixture (13) of the enantiomers onto the support material (15).

Figure 2:
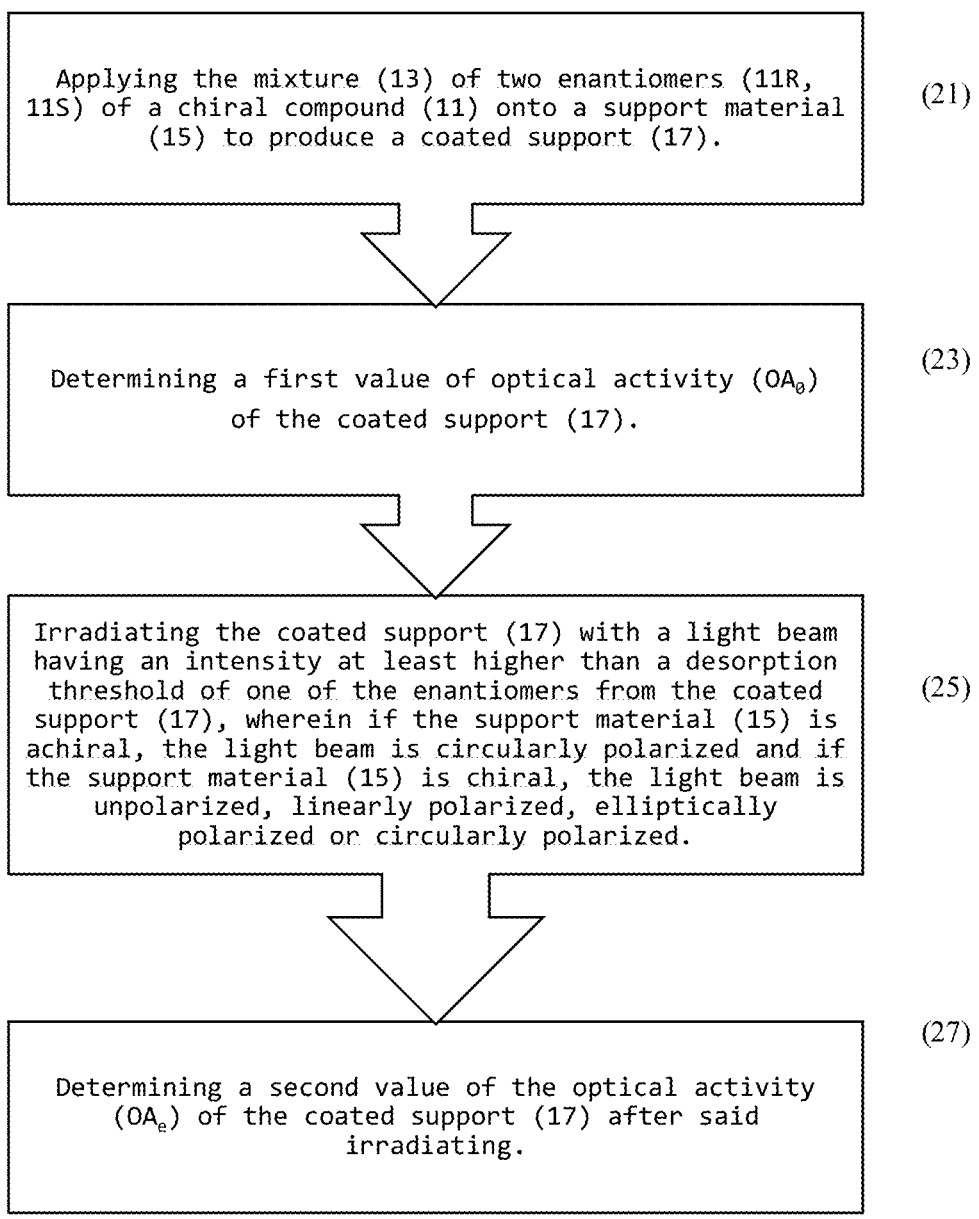
FIG. 2 shows a block diagram of a method for enantiomeric enrichment according to embodiments of the present invention.

Turning now to FIG. 2, the steps of the enantiomeric enrichment method according to the present invention are presented. According to the present invention, in a first step (21) a coated support (17) is produced. To this end a mixture (13) of the enantiomers is applied onto a support material (15). The mixture (13) of the enantiomers may be applied onto the support material (15) by common surface coating methods such as spraying, spin coating, drop casting and dip coating, provided that the mixture (13) of the enantiomers is in form of a solution. In cases where the mixture (13) is in form of a powder or a solution, molecular evaporation is employed for applying the mixture onto the support material (17).

According to a second step (23) of the method of the present invention, following the preparation of the coated support (17), a first value of the optical activity ($OA_0$) of the coated support (17) is determined. The determined value serves as a reference point of the enantiomeric enrichment process. The first value of optical activity ($OA_0$) is determined either by linear chiroptical techniques, such as circular dichroism or optical rotation dispersion or by nonlinear chiroptical methods, such as second harmonic generation circular dichroism or second harmonic optical rotation. The choice of the method for determining the value of the optical activity of the coated support (17) may vary depending on the optical activity of the chiral compound (11). In general, nonlinear chiroptical techniques show a higher sensitivity compared to the linear techniques, while the linear chiroptical techniques are easier in implementation and interpretation.

According to a third step (25) of the method of the present invention, the coated support (17) is irradiated with a light beam that is intense enough to cause desorption of at least one of the enantiomers (11R, 11S) from the coated support (17). A sense of asymmetry is introduced in the system, that is, either the support material (15) is asymmetric while interacting with the two enantiomers (11R, 11S), or the light beam is asymmetric, i.e. circularly polarized. Accordingly, the polarization state of the light beam is tuned depending on the chosen support material (15). If the support material (15) is achiral, the light beam is circularly polarized, as otherwise the two enantiomers (11R, 11S) would be desorbed from the coated support (17) with identical rates. The handedness of the circularly polarized light beam is the only component that causes a distinction between the two enantiomers (11R, 11S) in the mixture (13). If the support material (15) is chiral, the light beam does not need to be circularly polarized as the two enantiomers (11R, 11S) will have different interaction with the support material (15). In this case, the light beam may be unpolarized, linearly polarized, elliptically polarized or circularly polarized. The interaction of the light beam with the coated support (17) can be enhanced if the wavelength of the light beam is tuned to be resonant with optical transitions in the chiral compound (11). This tuning can be performed either by a single photon process or by a multiphoton process. The step of irradiating (25) leads to the enantiomeric enrichment of the coated support (17) by causing desorption of the two enantiomers (11R, 11S) from the coated support (17) with different desorption rates. The enantiomeric enrichment is confirmed through a further step (27) by means of which a second value of the optical activity ($OA_e$) of the coated support (17), differing from the first value of the optical activity ($OA_0$) is determined.

Example 1

The features of the method according to the present invention will now be described by way of an example describing preferred techniques and experimental results. The example is provided for the purpose of illustrating the present invention and should not be construed as limiting the same.

A racemic mixture of BINOL (2,2"-dihydroxy-1,1"binaphthyl) molecules has been applied onto an achiral support material BK7 glass by molecular evaporation in order to produce a coated support. The coated glass support has been irradiated by a femtosecond (fs) laser system with 1 kHz repetition rate (pulse duration~20 to 50 fs, 0.6 to 2.5 µJ/pulse). Thereafter, second harmonic generation circular dichroism has been used to determine the anisotropy factor (optical activity) of the coated glass support.

Figure 3:
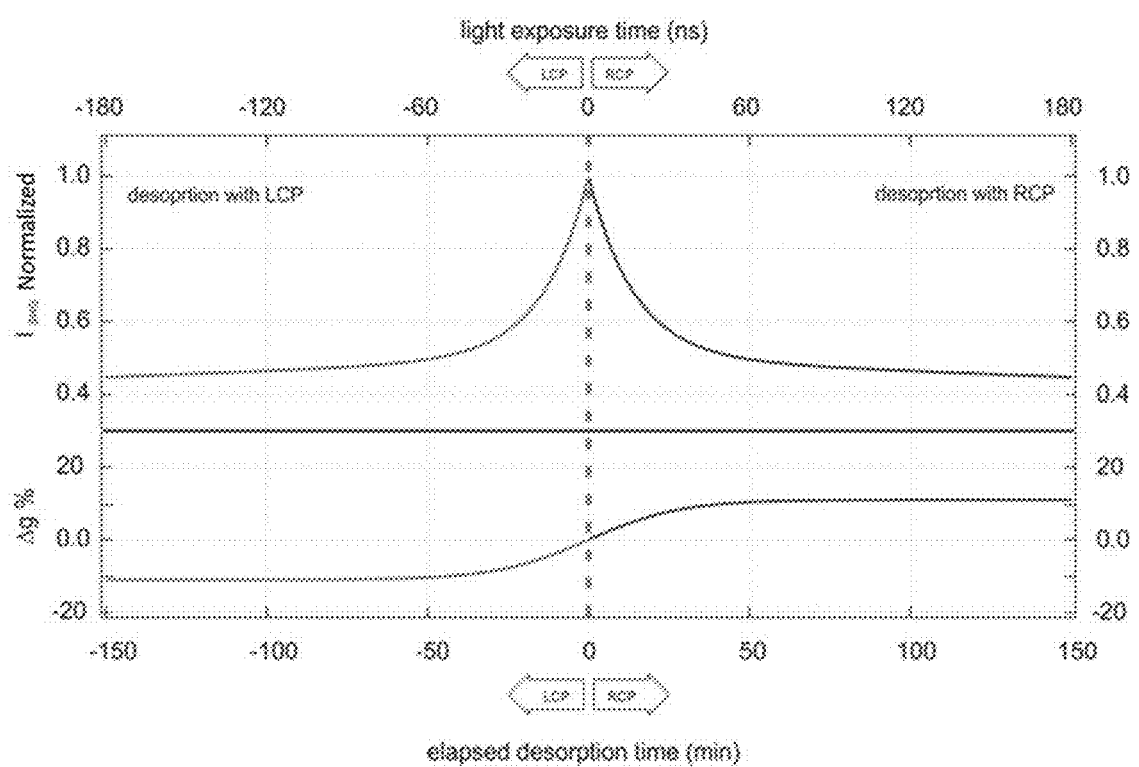
FIG. 3 shows in the top panel of the image the intensity of the generated second harmonic as a function of the irradiation time. The lower panel of the image shows the change of the optical activity of the coated glass surface as a function of the irradiation time.

The lower panel of FIG. 3 illustrates the value of the anisotropy factor ($\Delta g$) of the coated glass support as a function of irradiating time. The lower horizontal axis shows the time in terms of elapsed desorption time, while the top horizontal line shows the equivalent irradiating time in terms of light exposure time. As shown in Graph 1, a first value of anisotropy factor go of the coated glass support (i.e. before irradiation) at time 0 pertains to the $\Delta g=0$ (i.e. ee=0).

As an achiral support material (i.e. BK7 glass) has been used, the coated support material has been irradiated by circularly polarized light. The wavelength of the irradiation beam has been set to 650 nm so that its second harmonic (325 nm) is resonant with an optical transition in BINOL molecules.

Referring now to FIG. 3, the positive part of the time axis of the lower panel relates to elapsed desorption time with right-circularly polarized (RCP) light which increases from the time 0 to the right. The negative part of the time axis relates to left-circularly polarized (LCP) light (in which the absolute values also increase going from the time 0 to the left). In this example, the second value of the anisotropy factor has been determined after the coated support has been irradiated with 100000 laser pulses. That is, 100 s of elapsed desorption time is equivalent to 2 to 5 ns of light exposure time as indicated on the top time axis of FIG. 3. The step of irradiation (causing desorption) and subsequent determination of the optical activity have been repeated.

The top panel of FIG. 3 shows the intensity of the generated second harmonic signal as a function of desorption time. The result shows that firstly, desorption of the enantiomers has taken place at different desorption rates and that secondly, the total desorption of the enantiomers from the coated support is independent of the polarization of the light beam, i.e. it is similar for both RCP and LCP.

Referring to the lower panel of FIG. 3, the optical activity (here anisotropy factor $\Delta g$) of the coated support changes upon irradiation and takes opposite signs for opposite handedness of the irradiating light beam. Further, the optical activity of the coated support changes rapidly upon irradiating and reaches a plateau after some time (~30 minutes of elapsed desorption time or equivalently 1800000 laser pulses~36 ns of light exposure time). After this point of time, the optical activity of the coated support does not change any further (see lower panel of FIG. 3) although irradiating still causes further desorption of the enantiomers from the coated support (see the top panel of FIG. 3).

Any specific level of enantiomeric enrichment between the first value and the final value can be achieved by choosing an appropriate duration of irradiating time.

The top panel illustrates the intensity of the generated second harmonic provided by the BK7 glass coated by a racemic mixture of BINOL molecules as a function of the irradiating time, irradiated with a right circularly polarized light beam (from 0 to the right, positive values) and with a left circularly polarized light beam (from the 0 to the left, negative values). The intensity of the generated second harmonic is reduced when molecules desorb from the coated glass.

The lower panel illustrates the change in the optical activity of the coated glass as a function of the irradiating time irradiated with a right circularly polarized light beam (from 0 to the right, positive values) and with a left circularly polarized light beam (from 0 to the left, negative values).

The invention claimed is:

1. A method for enantiomeric enrichment of a mixture of two enantiomers of a chiral compound, the method comprising:
   applying the mixture of two enantiomers of a chiral compound onto a surface of a support material for producing a coated support;
   determining a first value of an optical activity of the coated support;
   irradiating the coated support with a light beam having an intensity at least higher than a desorption threshold of one of the enantiomers from the coated support, wherein, if the support material is achiral, the light beam is circularly polarized and, if the support material is chiral, the light beam is unpolarized, linearly polarized or circularly polarized; and
   determining a second value of the optical activity of the coated support after said irradiating, the second value of the optical activity differing from the first value of the optical activity.

2. The method according to claim 1, further comprising repeating said irradiating and said determining in order to obtain a final value of the optical activity of the coated support, which value corresponds to a given value of the optical activity.

3. The method according to claim 2, wherein the light beam has a wavelength that matches resonantly with an optical transition of the chiral compound, either by a single photon or by multiple photons.

4. The method according to claim 1, wherein said irradiating has a duration between 0.2 ns and 1000 s.

5. The method according to claim 1, wherein said irradiating comprises irradiating the coated support using by one of a light emitting diode, a pulsed laser or a continuous wave laser.

6. The method according to claim 1, wherein said determining includes determining the value of the optical activity by circular dichroism.

7. The method according to claim 1, wherein said applying includes an application of the enantiomeric mixture of two enantiomers by molecular evaporating.

8. The method according to claim 1, wherein the chiral support material belongs to the group of high Miller index surfaces of metals.

9. The method according to claim 1, wherein the achiral support material belongs to the group of amorphous solids of low Miller index surfaces of a metal.

10. The method according to claim 1, wherein the mixture of the two enantiomers is provided in powder.

11. The method according to claim 1, wherein the light beam has a wavelength that matches resonantly with an optical transition of the chiral compound by multiple photons.

12. The method according to claim 1, wherein said irradiating comprises irradiating the coated support using a pulsed laser or a continuous wave laser.

13. The method according to claim 1, wherein said irradiating comprises irradiating the coated support using a continuous wave laser.

14. The method according to claim 1, wherein said determining includes determining the value of the optical activity by optical rotation dispersion.

15. The method according to claim 1, wherein said determining includes determining the value of the optical activity by second harmonic generation circular dichroism.

16. The method according to claim 1, wherein said determining includes determining the value of the optical activity by second harmonic generation optical rotation.

17. The method according to claim 1, wherein said applying includes an application of the enantiomeric mixture of two enantiomers by spin coating.

18. The method according to claim 1, wherein said applying includes an application of the enantiomeric mixture of two enantiomers by dip coating.

19. The method according to claim 1, wherein said applying includes an application of the enantiomeric mixture of two enantiomers by drop casting.

20. The method according to claim 1, wherein the mixture of the two enantiomers is provided in liquid form.

\* \* \* \* \*